United States Patent
Anastassov et al.

(10) Patent No.: US 10,441,552 B2
(45) Date of Patent: Oct. 15, 2019

(54) ANTI-MICROBIAL COMPOSITION COMPRISING CANNABINOIDS

(71) Applicant: Axim Biotechnologies, Inc., New York, NY (US)

(72) Inventors: George E. Anastassov, New York, NY (US); Lekhram Changoer, Ridderkerk (NL); Philippus Anne Van Damme, Nijmegen (NL)

(73) Assignee: Axim Biotechnologies, Inc., New York, NY (US)

( * ) Notice: Subject to any disclaimer, the term of this patent is extended or adjusted under 35 U.S.C. 154(b) by 0 days.

(21) Appl. No.: 16/293,136

(22) Filed: Mar. 5, 2019

(65) Prior Publication Data

US 2019/0209487 A1    Jul. 11, 2019

Related U.S. Application Data

(63) Continuation of application No. 15/188,143, filed on Jun. 21, 2016, now abandoned.

(60) Provisional application No. 62/183,573, filed on Jun. 23, 2015.

(51) Int. Cl.

| | |
|---|---|
| *A61K 31/05* | (2006.01) |
| *A61K 9/00* | (2006.01) |
| *A61K 47/10* | (2017.01) |
| *A61K 9/12* | (2006.01) |
| *A61L 2/00* | (2006.01) |
| *A61L 2/18* | (2006.01) |
| *A61K 31/352* | (2006.01) |
| *A01N 31/16* | (2006.01) |
| *A61K 9/06* | (2006.01) |

(52) U.S. Cl.
CPC .............. *A61K 31/05* (2013.01); *A01N 31/16* (2013.01); *A61K 9/0014* (2013.01); *A61K 9/06* (2013.01); *A61K 9/12* (2013.01); *A61K 9/122* (2013.01); *A61K 31/352* (2013.01); *A61K 47/10* (2013.01); *A61L 2/0088* (2013.01); *A61L 2/18* (2013.01)

(58) Field of Classification Search
CPC .... A61K 31/05; A61K 31/352; A61K 9/0014; A61K 9/122; A61K 9/12; A61K 47/10
See application file for complete search history.

(56) References Cited

U.S. PATENT DOCUMENTS

| | | | | |
|---|---|---|---|---|
| 5,223,244 A | * | 6/1993 | Moro ..................... | A61K 8/046 424/45 |
| 2010/0130603 A1 | * | 5/2010 | Takahashi ............ | A61K 31/231 514/530 |

* cited by examiner

*Primary Examiner* — Angela C Brown-Pettigrew
(74) *Attorney, Agent, or Firm* — Khanh T. Glatzel; Premium IP Services, P.C.

(57) ABSTRACT

This invention discloses anti-bacterial and anti-fungal compositions in spray form, in cream form, in liquid form, and in powder form. The anti-bacterial and anti-fungal compositions comprise cannabinoids, specifically cannabidiol, cannabigerol, tetrahydrocannabinol, tetracannabidivarin, and/or cannabidivarin for anti-bacterial and anti-fungal activities. The anti-bacterial and anti-fungal compositions may be used to treat toe nail fungus, MRSA infection, herpes virus infection, tinea pedis, burn wound infections, sun burns, diabetic infections, eczema, impetigo, dermatophytosis, psoriasis, itchy skin, atopic dermatitis, dandruff, and general topical infections.

8 Claims, No Drawings

ANTI-MICROBIAL COMPOSITION COMPRISING CANNABINOIDS

CROSS-REFERENCE TO RELATED APPLICATIONS

This application is a continuation of U.S. application Ser. No. 15/188,143, filed Jun. 21, 2016, which claims the benefit of U.S. Provisional Application No. 62/183,573, filed Jun. 23, 2015. Each of the above referenced patent application is incorporated by reference in its entirety.

BACKGROUND OF THE INVENTION

Field of the Invention

This invention relates to anti-microbial, in particular anti-bacterial and anti-fungal compositions and the topical application of such compositions for the prevention and/or treatment of bacterial and fungal infections on the skin. The compositions comprise cannabinoids, specifically cannabigerol and/or cannabidiol, which are non-psychoactive phytocannabinoids. The composition is anti-microbial spray, antibiotic cream, antifungal cream, or anti-microbial liquid.

Description of the Related Technology

The cannabis plant has many naturally occurring substances that are of great interest in the fields of science and medicine. Isolated compounds from the cannabis plant include $\Delta^9$-tetrahydrocannabinol (THC), cannabidiol (CBD), cannabichromene (CBC), cannabigerol (CBG), cannabinol (CBN), cannabidivarin (CBDV), among other compounds. While THC has psychoactive effects, CBD, CBC, CBG, and CBDV do not. Isolated compounds from the cannabis plant are called cannabinoids. There are a total of eighty-five (85) cannabinoids that have been isolated from the cannabis plant. Many researchers have confirmed the medicinal value of cannabinoids. Cannabinoids have been investigated for possible treatment of seizures, nausea, vomiting, lack of appetite, pain, arthritis, inflammation, and other conditions.

Cannabinoids can be isolated by extraction or cold pressing from cannabis plants. Plants in the cannabis genus include *Cannabis sativa, Cannabis ruderalis*, and *Cannabis indica*. These plants are the natural sources of cannabinoids. Cannabinoids are also available in synthetic forms. Methods to synthesize cannabinoids in lab settings were discovered and are still currently practiced. Synthetic cannabinoids are more targeted, in that the synthetic compound usually comes isolated without other cannabinoids mixed in.

Nabilone (racemic(6aR,10aR)-1-hydroxy-6,6-dimethyl-3-(2-methyloctan-2-yl)-7,8,10,10a-tetrahydro-6H-benzo[c]chromen-9(6aH)-one), a synthetic cannabinoid, is believed to have fewer undesired side effects than THC. Nabilone mimics the chemical compound structure of THC. THC also exists in synthetic form under the name Dronabinol ((−)-(6aR,10aR)-6,6,9-trimethyl-3-pentyl-6a, 7,8,10a-tetrahydro-6H-benzo[c]chromen-1-ol)). These synthetic cannabinoids are sold for food supplement purposes and are being investigated for medicinal purposes. The U.S. Food and Drug Administration approved nabilone for treatment of chemotherapy-induced nausea and vomiting. In the United States, nabilone is marketed under the name Cesamet®.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. CBG has the IUPAC nomenclature of 2-[(2E)-3,7-dimethylocta-2,6-dienyl]-5-pentyl-benzene-1,3-diol. These are among the most prominent compounds in the family of compounds extracted from the cannabis plant referred to as cannabinoids.

Cannabidiol is a major phytocannabinoid, accounting for up to 40% of the plant's extract. CBD is a CB-1 receptor antagonist, while THC is a CB-1 receptor agonist. A 2010 research found that cannabis strains with higher concentration of CBD did not produce the short-term memory impairment normally seen in high THC cannabis strains, a characteristic attributed to the CB-1 receptor antagonist nature of CBD. CBD is considered to have a wider scope of medical applications than THC.

Because it is a relatively unknown cannabinoid, cannabigerol (CBG) remains understudied and its effects are only just starting to become clear. CBG is a non-psychoactive cannabinoid found in the cannabis plant. All cannabinoids in the early stage of the cannabis plant's life begins as CBG. CBG is found in higher concentrations in hemp plants as opposed to marijuana plants, which are grown to have higher concentrations of tetrahydrocannabinol (THC). CBG has been found to act as a high affinity $\alpha_2$-adrenergic receptor agonist, a moderate affinity 5-$HT_{1A}$ receptor antagonist, and a low affinity $CB_1$ receptor antagonist. It binds with the $CB_2$ receptor, but it is currently unknown whether it acts as an agonist or antagonist.

Cannabis abuse can occur among chronic users, especially when raw plant materials are consumed by smoking. Collectively, this abuse is referred to as cannabis use disorder. Discontinuance of cannabis consumption can result in withdrawal symptoms. However, some cannabinoids, such as CBD, may be useful in treating cannabis use disorder.

Anti-bacterial products are used to kill, repress the growth of, or repress the reproduction of bacteria. There are a number of topical anti-bacterial products on the market, including soap, hand sanitizer liquid, hand wipes, skin cream, spray, and eye drops. However, many of these existing products contain triclosan or triclocarban, ingredients criticized for having unanticipated effects on hormones and contributing to bacterial resistance. There is a demand for topical anti-microbial products without triclosan in order to avoid undesirable negative hormonal effects. The anti-microbial product has effects against difficult to treat bacteria, such as Methicillin-resistant *Staphylococcus aureus* (MRSA), as well as viruses and fungi.

SUMMARY

This invention generally relates to anti-microbial compositions comprising cannabinoids for use on human skin and/or nails, and for use on other non-living surfaces in frequent contact with humans. The anti-microbial composition comprises at least one cannabinoid at 2% to 5% by weight of the total composition. Cannabinoids used in this invention are either natural or synthetic. The cannabinoid anti-microbial composition is formulated as a spray, a gel, a cream, or a liquid.

In this invention, there is provided an anti-microbial in cream form comprising:
  at least one cannabinoid at 2% to 5% by weight of the total composition selected from the group consisting of cannabidiol, cannabigerol, tetrahydrocannabinol, cannabidivarin, and tetrahydrocannabivarin;

at least one alcoholic solvent at 20% to 40% by weight of the total composition selected from the group consisting of ethanol and isopropyl alcohol;

a humectant at 1% to 5% by weight of the total composition selected from the group consisting of glycerin, hyaluronic acid, lacto-ceramide, hydrolyzed keratin protein, and hydrolyzed collagen protein;

an emulsifier at 2% to 15% by weight of the total composition selected from the group consisting of PEG 40 hydrogenated castor oil, disodium PEG-4-cocoamido MIPA sulfosuccinate, lauryl glucoside, and sodium lauroamphoacetate; and water at 30% to 50% by weight of the total composition.

The anti-microbial composition in cream form may further comprise a binding agent selected from the group consisting of alginic acid, ammonium alginate, calcium caseinate, calcium sulfate hydrate, polyvinyl acetate, polyacrylic acid, polyisobutylene, potassium alginate, propylene glycol alginate, and polyvinylpyrrolidone at 5% to 20% by weight of the total composition.

The anti-microbial composition in cream form may further comprise a skin conditioning agent selected from the group consisting of amodimethicone, alkyl benzoate, caprylyl glycol, cetyl palminate, cyclo-dimethicone, dimethicone 500, dimethicone satin, ethylhexyl glycerin, iso-dimethicone copolymer, isododecane, isoeicosane, isolanolin, lanolin alcohol, octyldodecanol, PEG-8 dimethicone, and polyamide 3 at 0.1% to 2% by weight of the total composition.

The anti-microbial composition in cream form may further comprise a fragrance.

In this invention, there is provided an anti-microbial in spray form comprising:

at least one cannabinoid at 2% to 5% by weight of the total composition selected from the group consisting of cannabidiol, cannabigerol, tetrahydrocannabinol, cannabidivarin, and tetrahydrocannabivarin;

a humectant at 1% to 5% by weight of the total composition selected from the group consisting of glycerin, hyaluronic acid, lacto-ceramide, hydrolyzed keratin protein, and hydrolyzed collagen protein;

an emulsifier at 2% to 15% by weight of the total composition selected from the group consisting of PEG 40 hydrogenated castor oil, disodium PEG-4-cocoamido MIPA sulfosuccinate, lauryl glucoside, methyl gluceth-10, and sodium lauroamphoacetate;

at least one alcohol at 30% to 45% by weight of the total composition selected from the group consisting of ethanol and isopropyl alcohol; and water at 30% to 50% by weight of the total composition.

The anti-microbial in spray form may further comprise a chelating agent present at 0.05% to 0.5% by weight of the total composition selected from the group consisting of disodium gluconate, disodium EDTA, tetrasodium EDTA, and tetrasodium glutamate diacetate.

The anti-microbial in spray form may further comprise a skin conditioning agent present at 0.1% to 2% by weight of the total composition selected from the group consisting of amodimethicone, alkyl benzoate, caprylyl glycol, cetyl palminate, cyclo-dimethicone, dimethicone 500, dimethicone satin, ethylhexyl glycerin, iso-dimethicone copolymer, isododecane, isoeicosane, isolanolin, lanolin alcohol, octyldodecanol, PEG-8 dimethicone, and polyamide 3.

The anti-microbial in spray form may further comprise a fragrance.

In this invention, there is provided an anti-microbial liquid comprising:

at least one cannabinoid at 5% to 10% by weight of the total composition selected from the group consisting of cannabidiol, cannabigerol, tetrahydrocannabinol, cannabidivarin, and tetrahydrocannabivarin;

a surfactant at 3% to 10% by weight of the total composition selected from the group consisting of sodium lauryl sulfate, ammonium lauryl sulfate, sodium laureth sulfate, and sodium myreth sulfate;

at least one alcohol at 30% to 45% by weight of the total composition selected from the group consisting of ethanol or isopropyl alcohol; and water at 35% to 55% by weight of the total composition.

In this invention, there is provided an anti-microbial powder comprising:

at least one cannabinoid at 5% to 10% by weight of the total composition selected from the group consisting of cannabidiol, cannabigerol, tetrahydrocannabinol, cannabidivarin, and tetrahydrocannabivarin;

at least one preservative at 0.2% to 1.5% by weight of the total composition selected from the group consisting of butylhydroxytoluene, phenoxyethanol, paraben, and potassium sorbate;

at least one emollient at 3% to 20% by weight of the total composition selected from the group consisting of dimethylpolysiloxane, isopropyl myristate, amodimethicone, cetyl palmitate, cyclomethicone, dimethicone 500, and isododecane; and a powder comprising talc and hydrated silica at 20% to 90% by weight of the total composition.

The anti-microbial powder may further comprise:

at least one alcohol at 20% to 80% by weight of the total composition selected from the group consisting of ethanol and isopropyl alcohol; and at least one propellant solvent at 20% to 70% by weight of the total composition selected from the group consisting of butane, isobutane, propane, pentane, and dimethyl ether.

The anti-microbial powder may be packaged in an aerosol can.

In this invention, there is further provided a method to make an anti-microbial composition comprising the steps of:

dissolving at least one solid cannabinoid into an alcohol to form a solution;

adding at least one of an emulsifier, a humectant, a chelating agent, a binding agent, or a skin conditioning agent to the solution;

stirring the solution;

adding water to the solution; and stirring the solution.

The method to make an anti-microbial composition may further comprise the steps of adding a fragrance to the solution and adjusting the solution's pH to 6.

In this invention, there is further provided a method to make an anti-microbial powder comprising the steps of:

dissolving at least one solid cannabinoid into an alcohol to form a solution;

adding at least one emollient and at least one preservative into the solution from the first step;

adding the solution from the second step into a powder comprising talc and hydrated silica to form a powder;

mixing the powder mixture in a shear mixer;

adding the powder into an aerosol can; and adding at least one propellant selected from the group consisting of butane, isobutane, propane, pentane, and dimethyl ether.

The method to make an anti-microbial powder may further comprise the step of removing the alcohol by vacuum.

In this invention, there is further provided a method to disinfect a surface comprising the steps of:
applying an effective amount of a composition according to claim 1 to a surface; and
leaving the composition on the surface for at least 3 minutes,
wherein the surface is either mammal skin or non-living surfaces.

In this invention, there is further provided a method to treat an infection on mammal skin comprising the steps of:
applying an therapeutically effective amount of a composition according to claim 1 to the skin; and
leaving the composition on the skin for at least 3 minutes,
wherein the infection is selected from the group consisting of toe nail fungus, MRSA infection, herpes virus infection, tinea pedis, burn wound infections, sun burns, diabetic infections, eczema, impetigo, dermatophytosis, psoriasis, itchy skin, atopic dermatitis, dandruff, and general topical infections.

Abbreviations

CBC: Cannabichromene
CBD: Cannabidiol
CBDV: Cannabidivarin
CBG: Cannabigerol
CBN: Cannabinol
EDTA: Ethylenediaminetetraacetic acid
IUPAC: International Union of Pure and Applied Chemistry
MRSA: Methicillin-resistant *Staphylococcus aureus*
PEG: Polyethylene glycol
THC: Tetrahydrocannabinol
THCV: Tetrahydrocannabidivarin

DETAILED DESCRIPTION OF CERTAIN INVENTIVE EMBODIMENTS

This present invention is capable of being embodied in various forms. The description below of several embodiments is made with the understanding that the present disclosure is to be considered as an exemplification of the claimed subject matter, and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in their non-limiting sense to mean those items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more."

The word "cannabinoid" used in this description, claims, and other conjugations is used to mean any compound that interacts with a cannabinoid receptor and other cannabinoid mimetics, including, but not limited to, certain tetrahydropyran analogs ($\Delta^9$-tetrahydrocannabinol, $\Delta^8$-tetrahydrocannabinol, 6,6,9-trimethyl-3-pentyl-6H-dibenzo[b,d]pyran-1-ol, 3-(1,1-dimethylheptyl)-6,6a7,8,10,10a-hexahydro-1-1hydroxy-6,6-dimethyl-9H-dibenzo[b,d]pyran-9-ol, (−)-(3 S,4 S)-7-hydroxy-delta-6-tetrahydrocannabinol-1,1-dimethylheptyl, (+)-(3 S,4S)-7-hydroxy-$\Delta$-6-tetrahydrocannabinol, and $\Delta^8$-tetrahydrocannabinol-11-oic acid); certain piperidine analogs (e.g., (−)-(6S,6aR,9R,10aR)-5,6,6a,7,8,9,10,10a-octahydro-6-methyl-1-3-[(R)-1-methyl-4-phenylbutoxy]-1,9-phenanthridinediol 1-acetate)); certain aminoalkylindole analogs (e.g., (R)-(+)-[2,3-dihydro-5-methyl-3-(4-morpholinyl-ethyl)-pyrrolo[1,2,3-de]-1,4-benzoxazin-6-yl]-1-naphthalenyl-methanone); certain open pyran-ring analogs (e.g., 2-[3-methyl-6-(1-methylethenyl-2-cyclohexen-1-yl]-5-pentyl-1,3-benzendi-ol, and 4-(1,1-dimethylheptyl)-2,3'-dihydroxy-6'-α-(3-hydroxypropyl)-1',-2',3',4',5',6'-hexahydrobiphenyl), their salts, solvates, metabolites, and metabolic precursors.

The word "cannabidiol" refers to cannabidiol and cannabidiol derivatives. As used in this application, cannabidiol is obtained from industrial hemp extract with a trace amount of THC or from cannabis extract using high-CBD cannabis cultivars.

The word "cannabigerol" refers to cannabigerol and cannabigerol derivatives. As used in this application, cannabigerol is industrial hemp extract with a trace amount of THC or from cannabis extract.

In embodiments, the anti-microbial composition may comprise at least one cannabinoid, such as CBD or CBG, or a combination of cannabinoids. Other cannabinoids suitable for use in this anti-microbial composition may be THC, CBN, CBDV, or THCV, among other cannabinoids. The total amount of cannabinoid in embodiments may be at 2% to 5% by weight of the total composition.

Cannabinoids as used in this preferred embodiment may be provided as crystallized cannabinoids in solid form. Solid cannabinoids may be obtained from natural sources by freeze drying and/or heating of cannabis oil or hemp oil. Alternatively, solid cannabinoids may be obtained from synthetic sources. Methods to synthesize cannabinoids are disclosed in Patent Application Publication US2010/0298579 by THC Pharm GmbH and this reference is included herein as a whole.

Cannabinoids may also be in oily form, as cannabis oil, hemp oil, or hashish oil. Due to the hydrophobic nature of the oily form, formulations for liquid anti-microbial compositions may face difficulties in distribution and/or shelf life challenges. In emulsion formulation such as anti-microbial gel or cream, oily forms of cannabinoid may be used without difficulties in dispersion. It is contemplated that cannabinoids provided in oily form may be used in the embodiments described herein.

Cannabinoids as used in these embodiments may be CBD, CBG, THC, CBDV, THCV, or other molecules within the cannabinoid family. A combination of cannabinoids may be used in these embodiments, such that the total amount of cannabinoids comprises the quantities as described.

In embodiments, the anti-microbial composition may be a gel or cream for topical application. Apart from at least one cannabinoid, the gel or cream may comprise a liquid base, which may comprise a mixture of water and an alcoholic solvent. The liquid base may provide the environment in which various components of the gel or cream may be emulsified. Alcohol may also contribute to anti-microbial activities of the gel or cream as a whole. The alcohol solvent as used in this embodiment may be either ethanol or isopropyl alcohol. A mixture of alcohols may also be used.

In these embodiments, water may comprise 30% to 50% of the total composition by weight. Alcohol solvent preferably may comprise 20% to 40% of the total composition by weight.

The anti-microbial gel or cream may further comprise a humectant to keep the gel or cream from drying out. A suitable humectant for this gel or cream may be selected from the group consisting of glycerin, hyaluronic acid, lacto-ceramide, hydrolyzed keratin protein, and hydrolyzed collagen protein. When the gel or cream is used on nails, hydrolyzed keratin protein may be used to promote the growth of nails. The humectant may be present in this anti-microbial gel or cream at 1% to 5% by weight of the total composition.

The gel or cream may further comprise an emulsifier to emulsify hydrophobic components such as cannabinoids. A suitable emulsifier for this gel or cream may be selected from the group consisting of PEG 40 hydrogenated castor oil, disodium PEG-4-cocoamido MIPA sulfosuccinate, lauryl glucoside, and sodium lauroamphoacetate. The emulsifier may be present in this anti-microbial gel or cream at 2% to 15% by weight of the total composition.

A binding agent may also be used in this formulation to create a smooth emulsion. Suitable binding agents for this gel or cream may be alginic acid, ammonium alginate, calcium caseinate, calcium sulfate hydrate, polyvinyl acetate, polyacrylic acid, polyisobutylene, potassium alginate, propylene glycol alginate, and polyvinylpyrrolidone. Other binding agents suitable for topical cream or gel may also be used. The binding agent may be present at 5% to 20% by weight of the total composition.

The gel or cream may further comprise skin conditioning agents to promote a healthy appearance of the skin. Suitable skin conditioning agents may be selected from the group consisting of amodimethicone, alkyl benzoate, caprylyl glycol, cetyl palmitate, cyclo-dimethicone, dimethicone 500, dimethicone satin, ethylhexyl glycerin, iso-dimethicone copolymer, isododecane, isoeicosane, isolanolin, lanolin alcohol, octyldodecanol, PEG-8 dimethicone, and polyamide 3. Other skin conditioning agents may also be used. The skin conditioning agent may be present at 0.1% to 2% by weight of the total composition.

To enhance aesthetic appeal, fragrance may be added to the gel or cream. Various scents may be used as preferred. Alternatively, fragrance may not be used for those who prefer non-fragranced products.

The anti-microbial gel or cream may be used for skin application in wounds and skin infections. Alternatively, this anti-microbial gel or cream may be used for treatment of toe nail fungus due to its anti-fungal properties.

In other embodiments, the anti-microbial composition may be an anti-microbial spray for topical use. This anti-microbial composition may be formulated to become an aerosol upon pump action. This anti-microbial spray may be used on skin or non-living surfaces.

In these embodiments, the anti-microbial composition may comprise at least one cannabinoid, preferably CBD or CBG, or a combination of cannabinoids. Other cannabinoids suitable for use in this anti-microbial composition may be THC, CBN, CBDV, or THCV, among other cannabinoids. The total amount of cannabinoid in these embodiments may be at 2% to 5% by weight of the total composition Apart from at least one cannabinoid, the spray may comprise a liquid base, which may comprise a mixture of water and an alcohol. The liquid base may provide the environment in which various components of the spray may be emulsified. Alcohol may also contribute to anti-microbial activities of the spray as a whole. Alcohol used in these embodiments may be either ethanol or isopropyl alcohol.

In these embodiments, water may comprise 30% to 50% of the total composition by weight. Alcohol may comprise 30% to 45% of the total composition by weight. The total weight of the liquid base may comprise between 75% and 90% by weight of the total spray composition.

The anti-microbial spray may further comprise an emulsifier to effectively blend hydrophobic and hydrophilic components of the spray. A suitable emulsifier for this spray may be selected from the group consisting of PEG 40 hydrogenated castor oil, disodium PEG-4-cocoamido MIPA sulfosuccinate, lauryl glucoside, methyl gluceth-10, and sodium lauroamphoacetate. The emulsifier may be present in this anti-microbial gel or cream at 2% to 15% by weight of the total composition.

The anti-microbial spray may further comprise a humectant to maintain the water content in the spray. A suitable humectant for this gel or cream may be selected from the group consisting of glycerin, hyaluronic acid, lacto-ceramide, hydrolyzed keratin protein, and hydrolyzed collagen protein. When the anti-microbial spray is used on nails, hydrolyzed keratin protein may be used to promote the growth of nail growth. The humectant may be present in this anti-microbial spray at 1% to 5% by weight of the total composition.

A chelating agent may be added into this anti-microbial spray to preserve stability and efficacy of the spray. Suitable chelating agents may be disodium gluconate, disodium EDTA, tetrasodium EDTA, tetrasodium glutamate diacetate, among other suitable chelating agents. The chelating agent is present in the anti-microbial spray at 0.05% to 0.5% by weight of the total spray composition.

The anti-microbial spray may further comprise skin conditioning agents to promote a healthy appearance of the skin. Suitable skin conditioning agents may be selected from the group consisting of amodimethicone, alkyl benzoate, caprylyl glycol, cetyl palmitate, cyclo-dimethicone, dimethicone 500, dimethicone satin, ethylhexyl glycerin, iso-dimethicone copolymer, isododecane, isoeicosane, isolanolin, lanolin alcohol, octyldodecanol, PEG-8 dimethicone, and polyamide 3. Other skin conditioning agents may also be used. The skin conditioning agent may be present at 0.1% to 2% by weight of the total composition.

To enhance aesthetic appeal of the spray, fragrance may be added. Fragrances with various scents may be used as preferred. Alternatively, fragrance may not be used for non-fragrance products.

The anti-microbial spray composition may be used to treat skin infections, including infections from wounds, infections from bacteria, and infections from fungus. This anti-microbial spray may be used on skin as well as nail surfaces where the infection site may be present. Moreover, the anti-microbial spray may also be used to spray non-living surfaces, including furniture, walls, and door surfaces.

In another preferred embodiment, the anti-microbial composition may be a liquid comprising cannabinoids that may be used as a hand cleaner liquid, incorporated into wet wipes for anti-microbial purposes, or used as a cleaning liquid for disinfection.

In this preferred embodiment, the anti-microbial liquid comprises a liquid base, which comprises water and alcohol, wherein other ingredients may be dissolved. Water may comprise between 35% and 55% of the total anti-microbial liquid composition. Alcohol may comprise between 30% and 45% of the total anti-microbial liquid composition. Alcohols suitable for use in this embodiment may be ethanol and isopropyl alcohol.

Cannabinoids may be present in this anti-microbial liquid at 5% to 10% by weight of the total anti-microbial liquid. At least one cannabinoid may be used, but a combination of cannabinoids may also be effective.

The anti-microbial liquid according to this embodiment may further comprise a surfactant. Surfactants may act to reduce surface tension in the liquid and enable easy emulsifying of the mixture as a whole. Suitable surfactants may be sodium lauryl sulfate, ammonium lauryl sulfate, sodium laureth sulfate, and sodium myreth sulfate, among others. The surfactant may be present in this embodiment at 3% to 10% by weight of the total anti-microbial liquid composition.

The cannabinoid anti-microbial liquid may be applied to human skin to kill bacteria. Alternatively, this liquid may be applied to non-living surfaces such as furniture surfaces, walls, doors and door knobs, etc. to disinfect. This liquid may be useful in high-risk environments, such as hospitals or cruise ships.

In embodiments, cannabinoids may be provided in solid form and dissolved into an alcohol to form the alcohol phase. Other hydrophilic components may be dissolved into water to form the water phase; then the two phases may be combined and stirred.

Alternatively, cannabinoids may be dissolved in an alcohol solvent. Other components such as emulsifiers, humectants, chelating agents, binding agents, or skin conditioning agents may be added into the alcohol solution and stirred. Lastly, water may be added and stirred until uniform. The emulsion's pH may be adjusted to 6.

In another preferred embodiment, the anti-microbial composition may be a powder. The anti-microbial powder may be formulated in a spray or in powder form to be directly applied on to the skin. This anti-microbial powder may be used on skin to treat various bacterial, viral, and fungal infections.

In this preferred embodiment, the anti-microbial powder may comprise at least one cannabinoid, preferably CBG, CBD, THC, CBDV, or THCV but any other cannabinoid or a combination of cannabinoids may be used. Cannabinoids may be present in this embodiment preferably at 2% to 10% by weight of the total composition. Cannabinoids as used in this embodiment may be in powder form.

The anti-microbial powder may further comprise a base powder, such as a mixture of talc and hydrated silica. The base powder may comprise 30% to 90% by weight of the total composition. To facilitate the distribution of cannabinoids in this base powder, an alcohol solvent may be used.

Alcohol may be present in this preferred embodiment at 5% to 30% by weight of the total composition. The alcohol solvent may be ethanol or isopropyl alcohol. Cannabinoids in powder form may be dissolved into the alcohol solvent and stirred until homogenous. Preservatives, fragrance, and emollients may be added into the cannabinoid-alcohol solution.

Suitable preservatives may be butylhydroxytoluene, phenoxyethanol, paraben, and potassium sorbate. Preservatives may be present in this composition at 0.2% to 1.5% by weight. Suitable emollients are dimethylpolysiloxane, isopropyl myristate, amodimethicone, cetyl palmitate, cyclomethicone, dimethicone 500, isododecane, among other suitable emollients. Emollients may be present at 3% to 20% by weight of the total composition.

In a shear mixer, the base powder may be mixed. Cannabinoid may be dissolved into alcohol, then other components, such as preservatives and emollients, may be added and stirred until clear. The alcohol-cannabinoid solution may then be added into the shear mixer for further mixing. Once the powder in the shear mixer is homogenous, it may be used for further formulation and/or packaging.

In an embodiment, the anti-microbial powder may be an aerosol spray. The powder mixed by the shear mixer as above may be added into an aerosol can at 5% to 15% by total volume of the can. A propellant solvent selected from the group consisting of butane, isobutane, propane, pentane, and dimethyl ether may be added to the can to make up approximately 100% of the can volume. The propellant may be present at 20% to 70% by weight of the total composition in the aerosol can. The aerosol spray may be used by activating the pump to spray the content onto the skin or any surfaces.

In another embodiment, the anti-microbial powder may be a powder for direct application to the infectious site. The cannabinoid powder from the shear mixer may be dried under vacuum at 60° C. until ethanol evaporates from the powder. The powder may be filled into sachets or containers and may be used for direct application to mammal skin and left for at least 3 minutes.

Apart from common anti-microbial uses, this cannabinoid anti-microbial composition may be used to treat toe nail fungus, MRSA infection, herpes virus infection, tinea pedis, burn wound infections, sun burns, diabetic infections, eczema, impetigo, dermatophytosis, psoriasis, itchy skin, atopic dermatitis, dandruff, and general topical infections on human skin. The cannabinoid anti-microbial composition may be applied to the infected site in therapeutically effective amounts and left on the skin for at least 3 minutes.

The cannabinoid anti-microbial composition may also be used to disinfect any surface. An effective amount of the cannabinoid anti-microbial composition may be applied to a surface and left on the surface for at least 3 minutes.

Specific formulation processes are provided in the below examples for several embodiments.

EXAMPLES

Example 1

Anti-Microbial Spray

| Ingredients | Percentage |
| --- | --- |
| Water | 45.600 |
| Ethanol | 40.000 |
| CBG (solid) | 5.000 |
| PEG 40 hydrogenated castor oil | 5.000 |
| Glycerin | 3.000 |
| Disodium gluconate | 0.200 |
| Methyl gluceth-10 | 0.200 |
| Ethylhexyl glycerin/phenoxyethanol | 0.500 |
| Fragrance | 0.500 |
| NaOH (pH adjustment) | qs |
| Total | 100.00 |

Ingredients are obtained according to the above percentage. CBG in solid form is dissolved in ethanol in a beaker by stirring. Add PEG-40 into the beaker and stir until uniform. Add the beaker's content into water in another container and stir the mixture until uniform. Add glycerin, disodium gluconate, methyl gluceth-10 and stir until the solution is clear. Add ethylhexyl glycerin and stir until uniform. Lastly, add fragrance and stir until clear. The mixture's pH is adjusted to pH=6.

Example 2

Anti-Microbial Cream

| Ingredients | Percentage |
| --- | --- |
| Water | 44.000 |
| Ethanol | 30.000 |
| CBG | 5.000 |
| PEG 40 hydrogenated castor oil | 7.000 |
| Glycerin | 3.000 |
| Polyvinylpyrrolidone | 10.000 |
| Ethylhexyl glycerin/phenoxyethanol | 0.500 |
| Fragrance | 0.500 |
| NaOH | qs |
| Total | 100.00 |

Ingredients are obtained according to the above percentage. Dissolve polyvinylpyrrolidone in water to form the water phase and set aside. Dissolve CBG in ethanol and stir until the solution is clear, add PEG 40 to form the ethanol phase and stir until the solution is clear. Add the water and ethanol phases together, then add glycerin and stir until the solution is clear. Add ethylhexyl glycerin/phenoxyethanol and stir until the solution is clear. Add fragrance as needed and stir until clear, then adjust pH to 6.

Example 3

Anti-Microbial Liquid (Hand Cleaner)

| Ingredients | Percentage |
| --- | --- |
| Aqua | 48.000 |
| Sodium lauryl sulphate | 5.000 |
| Ethanol | 40.000 |
| CBG | 7.000 |
| Total | 100.000 |

Ingredients are obtained according to the above percentage. CBG is dissolved in ethanol in a beaker and stirred. Add sodium laurylsulphate into the beaker and stir until the solution is clear. Add this solution in to water in another beaker and stir until clear. The resulting liquid is packaged for dispensing.

Example 4

Anti-Microbial Powder

| Ingredients | Percentage |
| --- | --- |
| Hydrated silica | 30 |
| Talc | 44 |
| Butylhydroxytoluene | 0.5 |
| Dimethyl polysiloxilane | 5 |
| Isopropyl myristate | 5 |
| Fragrance | 0.5 |
| Ethanol | 10 |
| CBG | 5 |
| Total | 100 |

Ingredients are obtained according to the above percentages. Dissolve CBG in ethanol in a beaker. Add butylhydroxytoluene, dimethylpolysiloxane, isopropyl myristate, and fragrance into the beaker, then stir until homogenous. In a shear mixer, add talc and hydrated silica then mix until homogenous. Add the beaker's content from above into the shear mixer and mix to obtain a homogenous powder.

The powder mixture from the shear mixer may be added into an aerosol can at 10% volume of the can. Add propane to fill the aerosol can, and the aerosol cannabinoid powder may be applied to infection sites.

Alternatively, powder from the shear mixer is dried under vacuum at 60° C. to evaporate the ethanol. The cannabinoid antibacterial powder may be used to apply to infection sites.

All references, including publications, patent applications, and patents cited herein are hereby incorporated by reference to the same extent as if each reference were individually and specifically indicated to be incorporated by reference and were set forth in its entirety herein.

It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

What is claimed is:

1. An anti-microbial powder for use on skin comprising:
cannabigerol at 2% to 10% by weight of the total composition;
butylhydroxytoluene as a preservative at 0.2% to 1.5% by weight of the total composition;
dimethylpolysiloxane as an emollient at 3% to 20% by weight of the total composition; and
a powder comprising talc and hydrated silica at 30% to 90% by weight of the total composition.

2. The anti-microbial powder for use on skin of claim 1, further comprising ethanol at 5% to 30% by weight of the total composition.

3. The anti-microbial powder for use on skin of claim 2, further comprising dimethyl ether as a propellant solvent at 20% to 70% by weight of the total composition.

4. The anti-microbial power for use on skin of claim 3, wherein the powder is packaged in an aerosol can.

5. The anti-microbial power for use on skin of claim 3, further comprising a fragrance.

6. The anti-microbial power for use on skin of claim 5, wherein the powder is packaged in an aerosol can.

7. An anti-microbial powder for use on skin comprising:
cannabigerol at 2% to 10% by weight of the total composition;
butylhydroxytoluene as a preservative at 0.2% to 1.5% by weight of the total composition;
dimethylpolysiloxane as an emollient at 3% to 20% by weight of the total composition;
a powder comprising talc and hydrated silica at 30% to 90% by weight of the total composition; and
dimethyl ether as a propellant solvent at 20% to 70% by weight of the total composition,
wherein the powder is packaged in an aerosol can.

8. The anti-microbial power for use on skin of claim 7, further comprising a fragrance.

\* \* \* \* \*